(12) United States Patent
Royer et al.

(10) Patent No.: US 9,283,310 B2
(45) Date of Patent: Mar. 15, 2016

(54) EXTRACORPOREAL BLOOD TREATMENT APPARATUS

(75) Inventors: Michel Royer, Trois-Ruisseaux (CA); Fabio Roncadi, Mirandola (IT)

(73) Assignee: GAMBRO LUNDIA AB, Lund (SE)

( * ) Notice: Subject to any disclaimer, the term of this patent is extended or adjusted under 35 U.S.C. 154(b) by 0 days.

(21) Appl. No.: 13/003,824

(22) PCT Filed: Jul. 15, 2009

(86) PCT No.: PCT/IB2009/006238
§ 371 (c)(1),
(2), (4) Date: Feb. 14, 2011

(87) PCT Pub. No.: WO2010/007501
PCT Pub. Date: Jan. 21, 2010

(65) Prior Publication Data
US 2011/0152739 A1    Jun. 23, 2011

(30) Foreign Application Priority Data
Jul. 16, 2008    (IT) ............... MI2008A1288

(51) Int. Cl.
A61M 37/00     (2006.01)
A61M 1/16      (2006.01)
A61M 1/36      (2006.01)

(52) U.S. Cl.
CPC ............... *A61M 1/16* (2013.01); *A61M 1/3639* (2013.01); *A61M 2205/505* (2013.01)

(58) Field of Classification Search
CPC   A61M 2205/505; A61M 1/16; A61M 1/3639
USPC .................................................. 604/4.01–10
See application file for complete search history.

(56) References Cited

U.S. PATENT DOCUMENTS

| | | | |
|---|---|---|---|
| 6,024,089 A | 2/2000 | Wallace et al. | |
| 6,143,181 A | 11/2000 | Falkvall et al. | |
| 6,641,533 B2 | 11/2003 | Causey, III et al. | |
| 6,738,052 B1 | 5/2004 | Manke et al. | |
| 6,775,577 B2 | 8/2004 | Crnkovich et al. | |
| 7,256,771 B2 | 8/2007 | Novak et al. | |
| 7,318,892 B2 * | 1/2008 | Connell et al. | 210/94 |
| 8,075,509 B2 * | 12/2011 | Molducci et al. | 604/6.09 |
| 8,246,566 B2 * | 8/2012 | Lannoy | 604/5.04 |
| 2001/0016056 A1 | 8/2001 | Westphal et al. | |

(Continued)

FOREIGN PATENT DOCUMENTS

DE    197 42 633 A1    4/1999
DE    100 13 666 A1    10/2001

(Continued)

*Primary Examiner* — Philip R Wiest
*Assistant Examiner* — Ariana Zimbouski
(74) *Attorney, Agent, or Firm* — Pearne & Gordon LLP

(57) ABSTRACT

In an extracorporeal blood treatment apparatus, a user interface (22) has a touch screen for displaying two bar-graphs (24) of pressures in the extracorporeal blood circuit. By touching a bar-graph three alpha-numeric values appear: a reference value (29), an upper safety interval (28) of the pressure, comprised between an upper limit value and the reference valve (29), and a lower interval value (30), comprised between the reference value and a lower limit value. The reference value is a measured pressure value. Four buttons also appear on the display for input of modifications to the upper interval and the lower interval. The setting of the total pressure safety interval is simple and immediate.

10 Claims, 7 Drawing Sheets

(56) References Cited

U.S. PATENT DOCUMENTS

| | | |
|---|---|---|
| 2002/0002326 A1 | 1/2002 | Causey, III et al. |
| 2002/0085952 A1 | 7/2002 | Ellingboe et al. |
| 2003/0018395 A1 | 1/2003 | Crnkovich et al. |
| 2004/0064080 A1 | 4/2004 | Cruz et al. |
| 2004/0158193 A1 | 8/2004 | Bui et al. |
| 2004/0193325 A1 | 9/2004 | Bonderud et al. |
| 2004/0227737 A1 | 11/2004 | Novak et al. |
| 2005/0084416 A1 | 4/2005 | Thomas |
| 2005/0085760 A1 | 4/2005 | Ware et al. |
| 2006/0106847 A1* | 5/2006 | Eckardt et al. ............... 707/101 |
| 2006/0195064 A1 | 8/2006 | Plahey et al. |
| 2006/0258985 A1 | 11/2006 | Russell |
| 2007/0083152 A1 | 4/2007 | Williams et al. |
| 2007/0093712 A1 | 4/2007 | Nemoto et al. |
| 2007/0112603 A1 | 5/2007 | Kauthen et al. |
| 2007/0138069 A1 | 6/2007 | Roncadi et al. |
| 2007/0235376 A1 | 10/2007 | Daniel |
| 2007/0249982 A1 | 10/2007 | Daniel |
| 2008/0077073 A1* | 3/2008 | Keenan et al. .................. 604/19 |
| 2008/0154170 A1 | 6/2008 | Lannoy |
| 2008/0189783 A1* | 8/2008 | Music et al. ..................... 726/17 |
| 2008/0231595 A1* | 9/2008 | Krantz et al. .................. 345/156 |
| 2008/0243373 A1* | 10/2008 | Cat et al. ....................... 701/207 |

FOREIGN PATENT DOCUMENTS

| | | |
|---|---|---|
| EP | 0 904 788 A1 | 3/1999 |
| EP | 0 969 892 | 1/2000 |
| EP | 1 638 628 | 3/2006 |
| WO | 98/41269 A1 | 9/1998 |
| WO | 03/099355 A2 | 12/2003 |
| WO | 2004/103442 A1 | 12/2004 |
| WO | 2006/128536 A2 | 12/2006 |
| WO | 2007/000427 A1 | 1/2007 |

* cited by examiner

EXTRACORPOREAL BLOOD TREATMENT APPARATUS

The invention relates to an extracorporeal blood treatment apparatus.

Specifically, though not exclusively, the invention can usefully be applied to a dialysis monitor for setting a safety interval of a parameter inherent to the treatment, such as for example a pressure in the extracorporeal blood circuit.

The prior art comprises document DE 10013666, which illustrates a device for setting and viewing limit value for a measured parameter, in particular the venous pressure, arterial pressure and trans-membrane pressure, in a hemodialysis apparatus. The device comprises a touch-screen by means of which can be selected the range of the safety value interval comprised between two threshold values, a maximum and minimum, of the considered parameter. The touch screen further enables, in the same monitor display, selection of the middle point of the safety interval.

The above-described prior art can be improved upon, especially from the point of view of rapidity and simplicity of use, and in particular also in relation to the clarity and immediacy of the setting mode of an interval of safety values.

An aim of the present invention is to provide a system for facilitating the setting of a safety interval value where the value relates to an operating setting of a medical apparatus, in particular an apparatus for extracorporeal blood treatment.

An advantage of the invention is to provide a system which enables entering and viewing, in a simple, clear and immediate way, set values for a measured value of an operating parameter of the medical apparatus.

A further advantage is to make available a system which can be used rapidly and with small operations on the part of a user.

A still further advantage is to give rise to a system thanks to which it is possible to reduce the risk of an erroneous or incorrect setting by an operator.

In particular the present invention enables setting a safety value relating to a parameter using as a reference value a measured value of the parameter. The reference value is advantageously represented clearly and evidently on a screen of the user interface.

These aims and others besides are all attained by the present invention as it is characterised by one or more of the appended claims. Thanks to the apparatus of the present invention, the user can set a safety value of an operating parameter of the apparatus via the use of clear and simple setting means, instantly understandable and readily usable. To this end the apparatus is provided with a user interface provided with a screen and selecting means for enabling a user to select, via the screen, a first safety value and a second safety value, in which the first safety value is equal to the range of an upper interval comprised between a limit safety value for the parameter and a reference value of the parameter, while the second safety value is equal to the range of a lower interval comprised between the reference value and a lower limit value for the parameter, where the reference value is a measured value of the parameter. In this way the user can set the whole safety interval (i.e. the interval comprised between the lower limit value and the upper limit value) while having present, clearly and immediately, a reference value coinciding with an effectively-measured value of the parameter for which the safety interval is to be set. The user can set the range of two partial intervals, i.e. the range of the interval above a real value of the parameter and the range of the interval below the real value, the two partial intervals, upper and lower, defining overall both the range and the position of the whole safety interval.

The user interface can comprise activating means for activating the selecting means on the monitor screen (the activating means can comprise, for example, one or more active buttons on a first region of the screen, while the selecting means can comprise, for example, one or more active buttons on a second region of the screen, different from the first region). In this case the reference value could be a measured value at a given moment in which, by operating on the activating means (for example by touching a button on the first region if the first region is of the type which is activatable by touch/proximity), the selecting means are made activatable (for example the active buttons are visualised on the second region of the screen), or a just-before measured value (within a predetermined preceding period of time) with respect to the moment of activation, or a value measured soon after and possibly updated according to a predetermined periodic interval. In this way the reference value corresponds to a real value, effectively measured at a relatively near moment to the performance of the setting/modification process of the safety interval.

In a specific embodiment, the selecting means comprise a view which displays an alpha-numeric representation (arabic numerals) of the first safety value (range of the upper interval), a reference value (real value, measured) and a second safety value (range of lower interval). By doing this the user recognises the values to be set clearly and immediately, and furthermore is able to compare them simply and directly with the reference value, thus reducing the risk of a wrong setting.

In a specific embodiment, the selecting means comprise input means for modifying the first safety value and the second safety value displayed on the screen. The input means can comprise, for example, at least an increase button for increasing and respectively a reducing button for reducing the first safety value. The buttons can appear on the screen together with the first safety value, or they can be displayed by activation of special activating means (for example by touching or by another method, of a button coinciding with the alpha-numeric icon representing the first safety value). The input means can also comprise, for example, at least an increase button and at least a decrease button for increasing and respectively decreasing the second safety value. In this case too the buttons can appear on the screen together with the second safety value, or can be visualised by activating special activating means (for example by activating, by touching or by another method, a button showing the alphanumeric icon representing the second safety value).

In a specific embodiment, input means are included for modifying the first and second safety values, which input means comprise four buttons, wherein a first button increases by a predetermined quantity both the first value and the second value, a second button reduces by a predetermined quantity both the first value and the second value, a third button increases by a predetermined quantity the first value and reduces by a predetermined quantity the second value, a fourth button increases by a predetermined quantity the second value and reduces by a predetermined quantity the first value. The input means can be visualised at the same time as the two safety values, or can be visualised successively, for example on activation of special activating means visualised on the screen at the same time as the two safety values. The activating means might comprise, for example, the same button icons that represent the two safety values.

In a specific embodiment, the selecting means comprise confirm means (for example a confirm button, optionally a touch-sensitive or proximity-sensitive button) to confirm the entering of a change in the first and/or the second safety values. The selecting means can optionally comprise cancel means (for example a cancelling button, optionally a touch- or proximity-sensitive button) for cancelling the actions performed by the selecting means and possibly also for cancelling the actual selecting means.

In a specific embodiment, the functioning parameter of the medical apparatus for which the safety values are set can be a parameter selected from among the following: an arterial pressure in a blood removal line from a patient, a venous pressure in a blood return line to the patient, a transmembrane pressure between the two sides of a semipermeable membrane of a blood treatment device.

Further characteristics and advantages of the present invention will better emerge from the detailed description that follows of at least an embodiment of the invention, illustrated by way of non-limiting example in the accompanying figures of the drawings.

The description will be made herein below with reference to the accompanying drawings, provided by way of non-limiting example.

Figure 1:
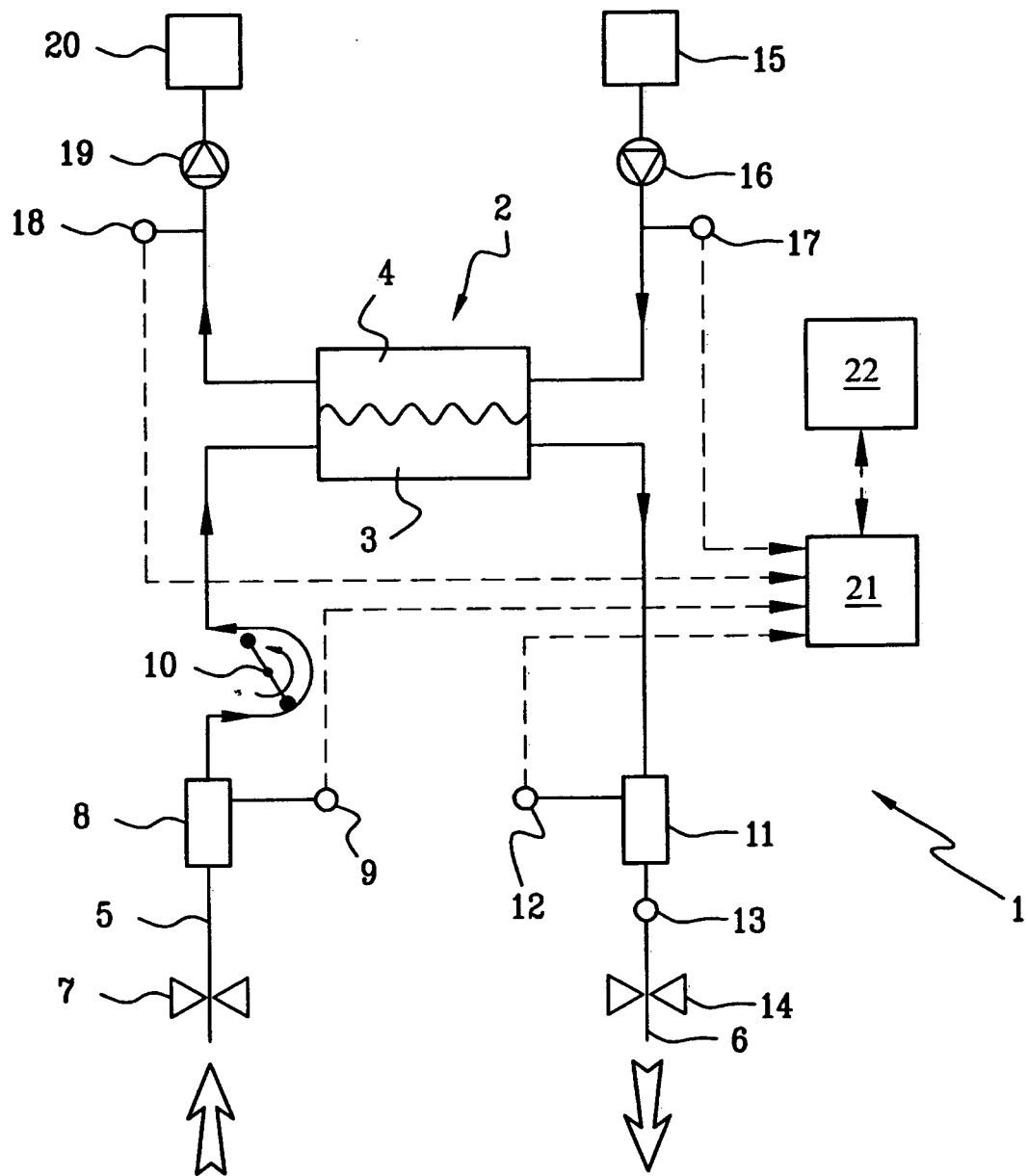
FIG. 1 is a first embodiment of a medical apparatus according to the present invention.

With reference to FIG. 1, 1 denotes in its entirety an extracorporeal blood treatment apparatus, as in FIG. 1, or any other apparatus of known type for performing hemodialysis, hemo (dia)filtration, hemoperfusion, plasma exchange, pure ultrafiltration, kidney failure treatment, etc.

The apparatus of FIG. 1 comprises a blood treatment device 2 of the membrane type, having a blood chamber 3 and a fluid chamber 4, separated from one another by a semipermeable membrane.

An extracorporeal blood circuit has a removal line 5 (arterial line) for sending blood from an individual to the blood chamber 3, and a return line 6 for returning the blood from the blood chamber 3 to the patient. The extracorporeal blood circuit can comprise any one of the circuits of known type used in a hemodialysis or hemo(dia)filtration apparatus. FIG. 1 illustrates only some of the elements the extracorporeal blood circuit can be equipped with, such as in particular an arterial clamp 7, an arterial chamber 8 for air-blood separation, a pre-pump arterial pressure sensor 9, a blood pump 10, a venous chamber 11 for air-blood separation, a venous pressure sensor 12, an air bubble sensor 13, a venous clamp 14.

A fluid circuit is connected to the fluid chamber 4. The fluid circuit can comprise any one of the fluid circuits (for supplying and/or discharging one or more treatment fluids and/or discharging to/from the membrane treatment device) of known type used in a hemodialysis device or a hemo(dia) filtration device. FIG. 1 illustrates only some of the elements with which the fluid circuit can be provided, such as in particular a treatment fluid source 15, a pre-chamber supply pump 16, a pre-chamber pressure sensor 17, a post-chamber pressure sensor 18, a post-chamber discharge pump 19, a drainage 20 for a discharge fluid. Other elements of a fluid circuit of a medical apparatus (for hemodialysis and/or hemo (dia)filtration) can be provided, of known type and not illustrated, such as for example a fluid balancing system for control of patient weight loss, a disinfection system of the fluid circuit, a heating and/or degassing system of the fluid in the fluid circuit, etc.

Both the extracorporeal blood circuit and the fluid circuit can be provided with other sensors, apart from those already illustrated in FIG. 1, for measuring the value of various operating parameters in the extracorporeal blood circuit and/or in the fluid circuit, such as for example a hematocrit sensor in the blood circuit, a blood loss sensor in the fluid circuit or BLD (Blood Leak Detrector), a pH sensor in the fluid circuit, one or more conductivity sensors in the fluid circuit, a patient sensor (normally a blood presence sensor) in the blood circuit, etc.

The apparatus is provided with a control unit 21 configured to receive monitoring signals from various sensors of the apparatus and to send command signals to the various actuators of the apparatus. A user interface 22, provided with a screen and various other elements (of known type and not illustrated) for enabling communication between the user and the control unit 21, is connected to the control unit 21 and thus, through the unit 21, to the various sensors and actuators of the apparatus 1.

FIGS. 2 to 7 illustrated in greater detail the operating mode of the user interface 22. In the specific case the user interface is provided with a touch screen, although it is possible to use a non-touch screen or other known types besides, such as for example a multi-touch screen, i.e. a screen able to recognise more than a touch-point simultaneously, or with a screen that is operationally associated to a separate touch pad, etc. The user interface 22 comprises selecting means 23 (FIGS. 3 to 7) for enabling a user to select via the screen a first safety value and a second safety value of a parameter measured by one or more sensors of the apparatus. In the specific case the selecting means 23 enable two safety values to be set for the arterial pressure measured by the arterial pressure sensor 9 and two safety values to be set for the venous pressure measured by the venous pressure sensor 12. Each pair of safety values defines an interval of safety values (in the specific case an upper interval and a lower interval). It is possible to comprise setting safety values for other parameters apart from the arterial pressure and the venous pressure, such as for example the trans-membrane pressure (the pressure difference between the blood chamber 3 and the fluid chamber 4 calculated in a known way on the basis of signals supplied by one or more pressure sensors arranged on the extracorporeal blood circuit and by one or more pressure sensors arranged on the fluid circuit).

In the specific case, the arterial pressure and the venous pressure are each represented by a bar-graph 24 (see FIG. 2) which shows the current measured value (denoted by an arrow 25) and the safety interval 26 at present set. In the specific case of FIG. 2 the current measured value of the venous pressure is, purely by way of example, 47 mmHg, while the value of the arterial pressure is −53 mmHg. The current measured value can further be represented by a number (in arabic numerals) on a region 27 of the screen. The safety interval 26 is optionally shown by a portion of bar in a different colour from the rest of the bar. The safety interval 26 is defined by an upper limit value and a lower limit value. The safety interval 26 can be set by an operator, as will be explained more fully herein below.

The user interface 22 comprises activating means for activating the selecting means 23 on the screen. In the specific case the activating means comprise a touch region of the touch screen which, if touched, causes the selecting means 23 to appear on the screen. This region can comprise, as in the example, the bar graph 24 of the arterial pressure or the venous pressure. In other words, touching on the bar graph 24 of the arterial pressure or venous pressure activates the selecting means 23 of the safety interval of the arterial or venous pressure. The same can be done with any other icons representing the current measure value for other parameters, for example with the bar graph of the trans-membrane pressure.

Figure 2:
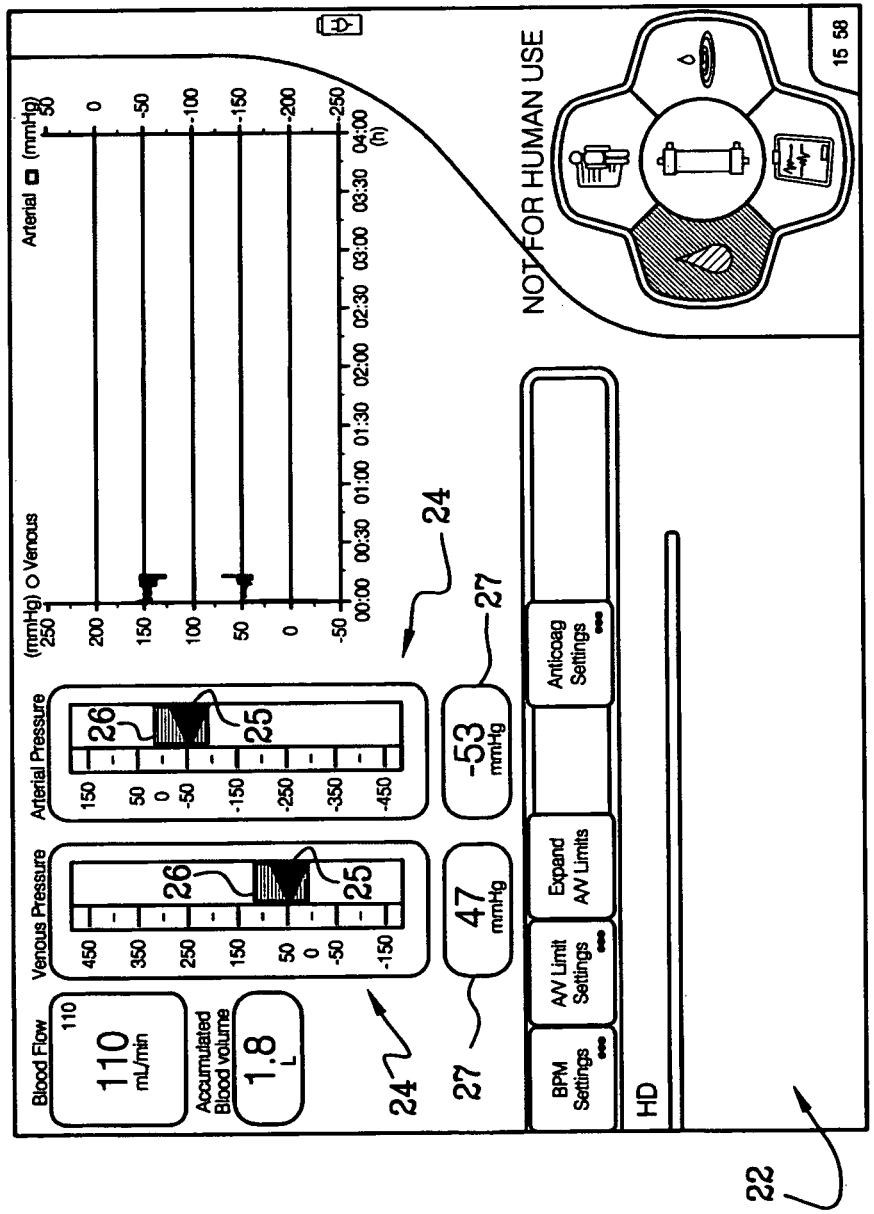
FIG. 2 is a user graphic interface of the apparatus of FIG. 1.
Figure 3:
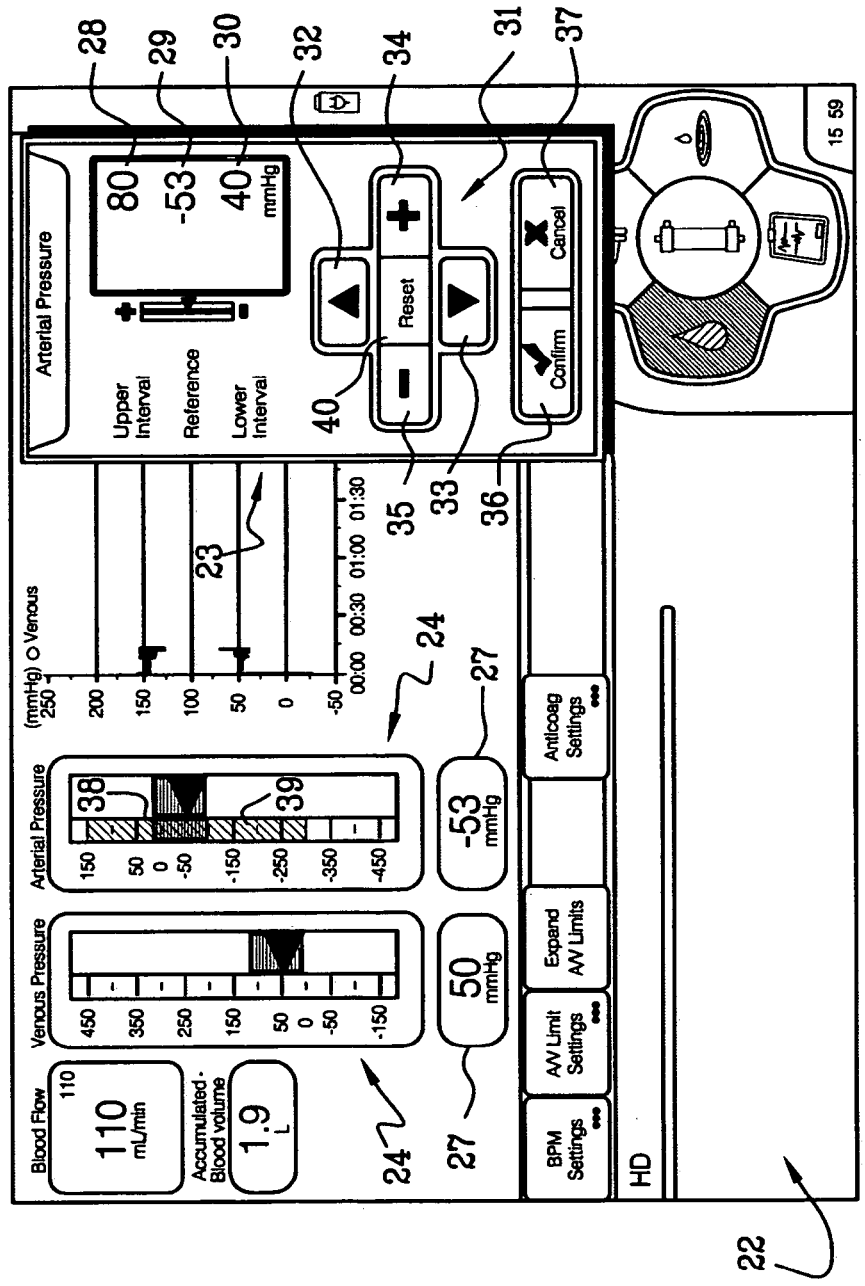
FIGS. 3 to 7 show the graphic interface of FIG. 2 in five different operating configurations.

With reference to the example in the accompanying figures, it can be seen that touching the bar-graph 24 of the arterial pressure in FIG. 2 activates a display which includes the selecting means 23 illustrated in FIG. 3 (high up on the right) in order to enable the selection/modification of the safety interval of the arterial pressure. It is possible for the activating means of the selecting means to comprise a further region of the touch screen (for example the region denoted by 27 in which the alphanumeric value (in arabic numerals) of the current measure of the parameter is shown, or a specially-generated region for enabling activation of the selecting means), or a button which can be activated or another activatable device external of the touch screen.

The selecting means 23 comprise a display on a region of the touch screen (optionally a different region from the one illustrating the activating means) comprising an alphanumeric representation (in arabic numerals) of the first safety value (upper interval 28 in FIGS. 3 to 7) of a reference value (reference 29 in FIGS. 3 to 7), and of a second safety value (lower interval 30). The first safety value is arranged above the reference value. The second safety value is arranged below the reference value.

Additionally or alternatively to the above-described selecting means 23, other selecting means provided with a graphic representation can be provided (for example having a bar-graph or another non-alphanumeric graphic representation) of the safety intervals. In particular a similar representation to the graphic representation 38 visualised on the activating means next to the bar-graph 24 (to the left of the graph in FIGS. 3 to 7) can be used. This graphic representation 38 exhibits a preview in graph form (a coloured bar having corresponding to the total safety interval which is modified in real-time by effect of the modifications performed with the selection means 23) of the settings in course performed using the selection means 23.

There is also a graphic representation 39 of an acceptable interval for the relative parameter (for example the arterial pressure) during the course of the treatment. This acceptable interval (wider than the safety interval 26) defines an upper limit and a lower limit allowed for the total safety limit 26. The treatment interval visualised via the graphic representation 39 will thus represent an interval including the safety interval 26. In particular the controller is set such that the safety interval 26 cannot completely exit from a treatment interval. The graphic representation 39 of the treatment interval will appear together with the graphic representation 38 previewing the safety interval and with the selection means 23 (on activation of the activating means 24). The graphic representation 39 comprises a bar coloured differently to the graphic representation bar 38, the two bars being at least partially superposed on one another.

The reference value is, optionally, a parameter value measured at the moment of activation of the selection means, or measured within a predetermined period of time preceding the moment of activation. In the specific case the reference value 29 is the value (−53 mmHg) which has been detected by the arterial sensor 9 at the moment of activation (illustrated in FIG. 2).

The reference value might also be a measured value of the parameter which is updated in real-time during the setting stages performed using the selection means 23.

The first safety value and the second safety value are the same as the width of an upper interval 28 and, respectively, a lower interval 30, in which the upper interval 28 is comprised between an upper limit value for the parameter and the reference value of the parameter, while the lower interval 30 is comprised between the reference value and a lower limit value for the parameter.

On activating the activating means (bar graph 24), the selecting means 23 will appear on the screen. FIG. 3 shows the selecting means 23 as they appear immediately after the activation of the activating means (bar graph 24) of FIG. 2. In the specific case, the selecting means 23 will appear with the current values in the upper interval 28 and the lower interval 30 (values which depend, as is obvious, on the current parameter value, for example the arterial pressure in FIG. 3, measured at that instant or very soon before, as well as the current setting, performed previously, relating to the safety interval). As mentioned, the reference value is a measured value of the parameter. In FIG. 3 the reference 29 is −53 mmHg, the upper interval 28 is 80 mmHg (so that the upper limit value of the total safety interval is effectively +27 mmHg), and the lower interval 30 is 40 mmHg (so that the lower limit value of the safety interval is effectively −93 mmHg).

The selecting means 23 further optionally comprise input means 31 for modifying the first safety value (upper interval 28) and the second safety value (lower interval 30) visualised on the screen. The input means 31 can optionally comprise at least an increase button for increasing the first safety value and a decrease button for reducing the first safety value. The input means can optionally comprise at least an increase button for increasing the second safety value and a decrease button for reducing the second safety value.

In the present specific case, the input means 31 comprise a positive displacement button 32 for the total safety interval; this button 32 can optionally comprise the pictogram of an arrow facing upwards or another pictogram representing the "increase" concept, or "movement upwards" concept, i.e. in the increasing direction. The arrow substantially indicates the positive displacement of the safety interval, i.e. in the sense of the incrementing of the values, both the upper limit and the lower limit (practically a translation in the positive direction of the safety interval without modification to the total range of the interval itself). This means that by effect of the touch on the positive displacement button 32 the upper interval 28 will increase (as the difference between the upper limit and the reference 29, which remains constant, will increase), while the lower interval 30 will diminish (as the difference between the lower limit and the reference 29, which remains constant, will diminish). The increase in the upper interval 28 is optionally equal to the reduction in the lower interval 30, as in the specific case.

Figure 4:
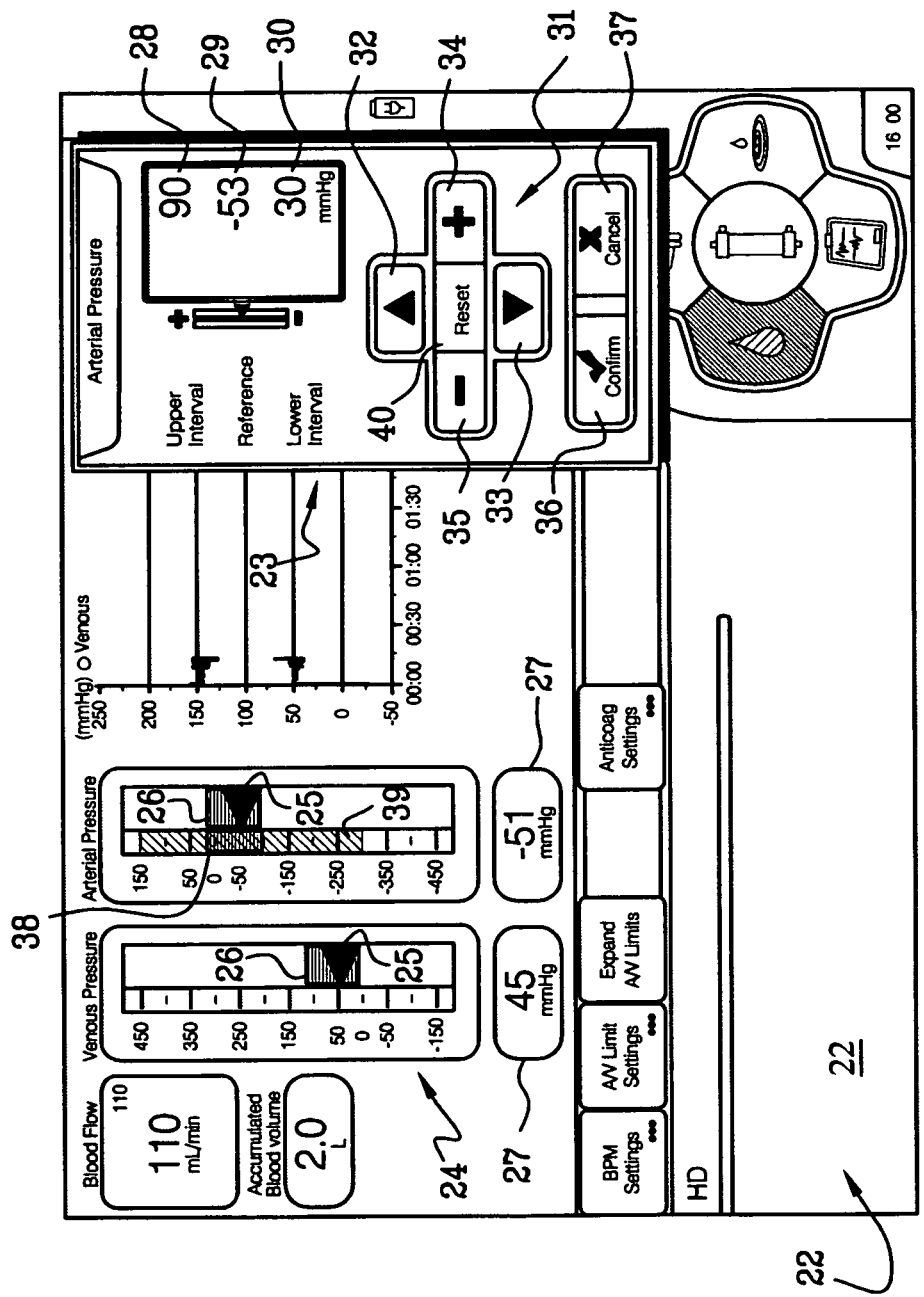

The effect of the activating of the button 32 is represented by the passage from the configuration of FIG. 3 to that of FIG. 4, from which a displacement of the overall interval for the arterial pressure obtains (i.e. in the increase direction) by a certain value predetermined by each touch, for example by 10 mmHg in the illustrated example. It can be noted that the preview graphic representation 38 of the safety interval is subject to a corresponding modification (with the aim of immediately visualising the proposed change in the interval before effective acceptance of such change) while the bar graph 26 and the arrow 25, which are representative of the situation at the moment of appearance of the selecting means 23 for effecting the modification of the safety interval remain the same. Note that the graphic representation 38 (preview) is arranged by the side of the graph 26, i.e. the graphic representation of the situation at the moment of activation of the selecting means 23.

The entity of the displacement (increase of the upper interval 28 and/or decrease of the lower interval 30) at each touch of the positive displacement button 32 of the total interval, which in the specific case is 10 mmHg, can be preset during the stage of configuration of the control unit and can also be modified subsequently according to requirements.

In the specific case of the passage from the initial configuration of FIG. 3 to the configuration of FIG. 4 (by effect of the activation of the positive displacement button 32), the upper interval 28 has changed from 80 mmHg to 90 mmHg (thus the upper limit of the safety interval will have changed from +27 mmHg to +37 mmHg, the reference 29 having stayed at −53 mmHg), while the lower interval 30 has passed from 40 mmHg to 30 mmHg, such that the lower limit of the total safety interval has been moved (increased) from −93 mmHg to −83 mmHg.

It is therefore obvious that the selecting means 23 enable an immediate visualisation of the upper and lower intervals with reference to the current value of the parameter.

In the specific case described herein, the input means 31 comprise a negative displacement button 33 of the total safety interval; this button 33 can optionally comprise the pictogram of an arrow directed downwards or another pictogram representing the concept of "decrease" or "displacement downwards" or "negative displacement" of the safety interval, i.e. total translation in the direction of decreasing of the values. This arrow in substance indicates the translation of the safety interval in the sense of decrease both of the upper limit and the lower limit (in practice an overall displacement of the safety interval without modifying the total range of the interval itself, but in an inverse direction with respect to the preceding case relating to the button 32). This means that, by effect of touching the negative displacement button 33, the upper interval 28 will diminish (as the difference between the upper limit and the reference 29, which remains constant, will diminish), while the lower interval 30 will increase (as the difference between the lower limit and the reference 29, which remains constant, will increase). The reduction of the upper interval 28 can optionally be equal to the increase of the lower interval 30. The effect of the activation of the button 33 can be, in substance and optionally, inverse with respect to that of the button 32, i.e. it will be a displacement of the overall safety interval for the arterial pressure downwards (i.e. in the lowering direction) by, for example 10 mmHg. In this case too the entity of the displacement of the whole safety interval (increase in the lower interval 30 and/or decrease in the upper interval 28) connected to each touch of the button 33 can be preset during the stage of configuration of the control unit and modified subsequently according to need.

Figure 5:
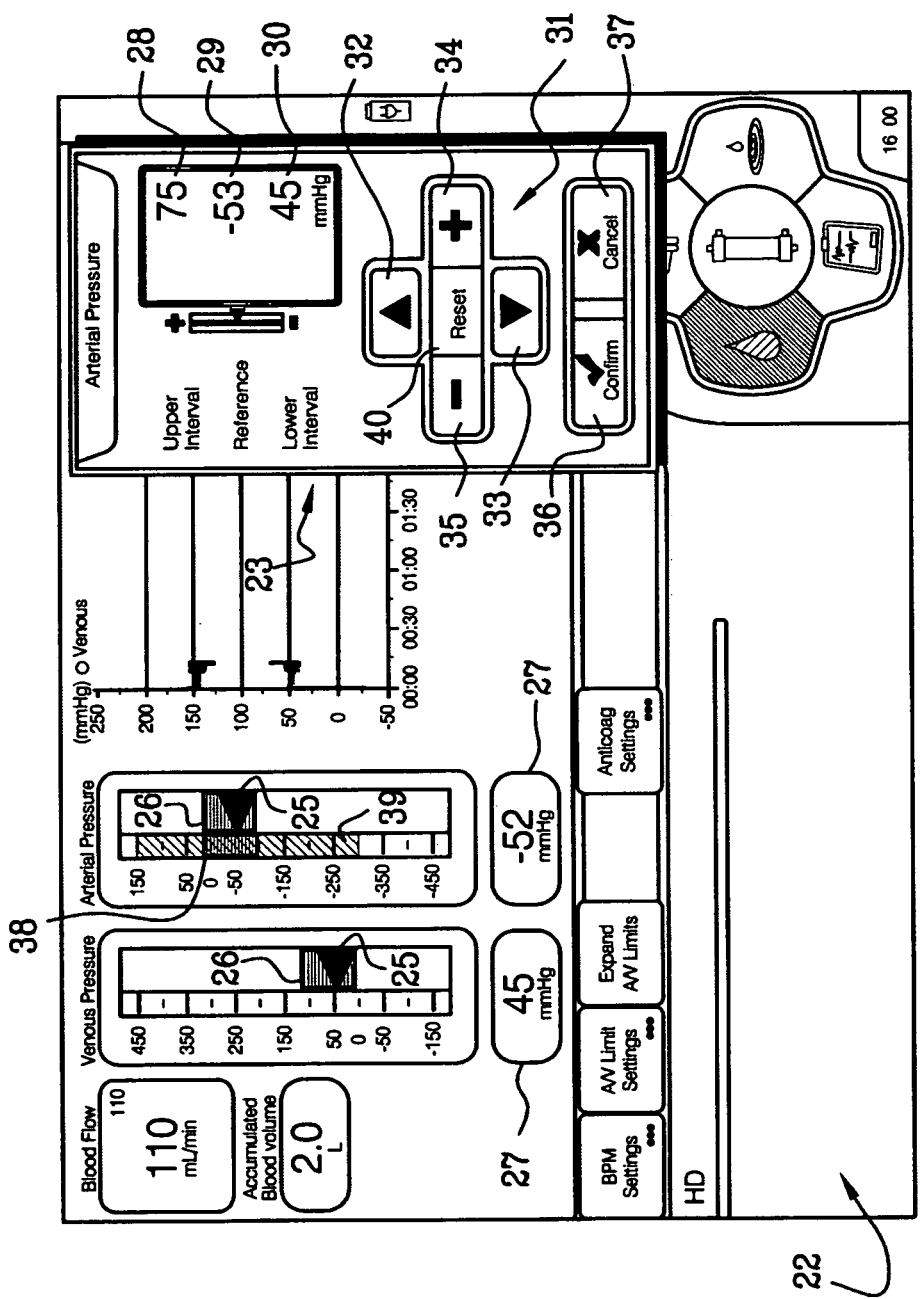
Figure 6:
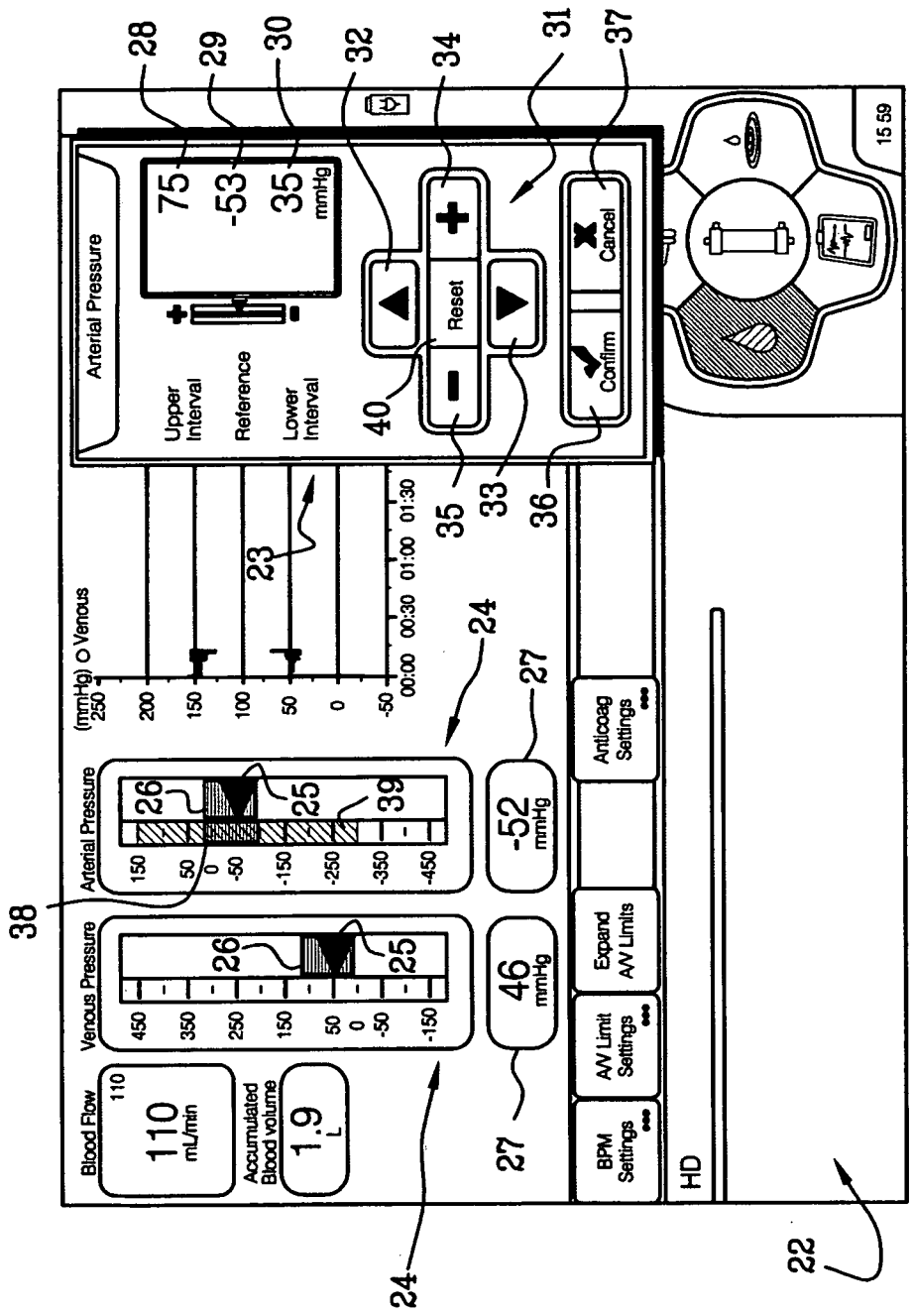
Figure 7:
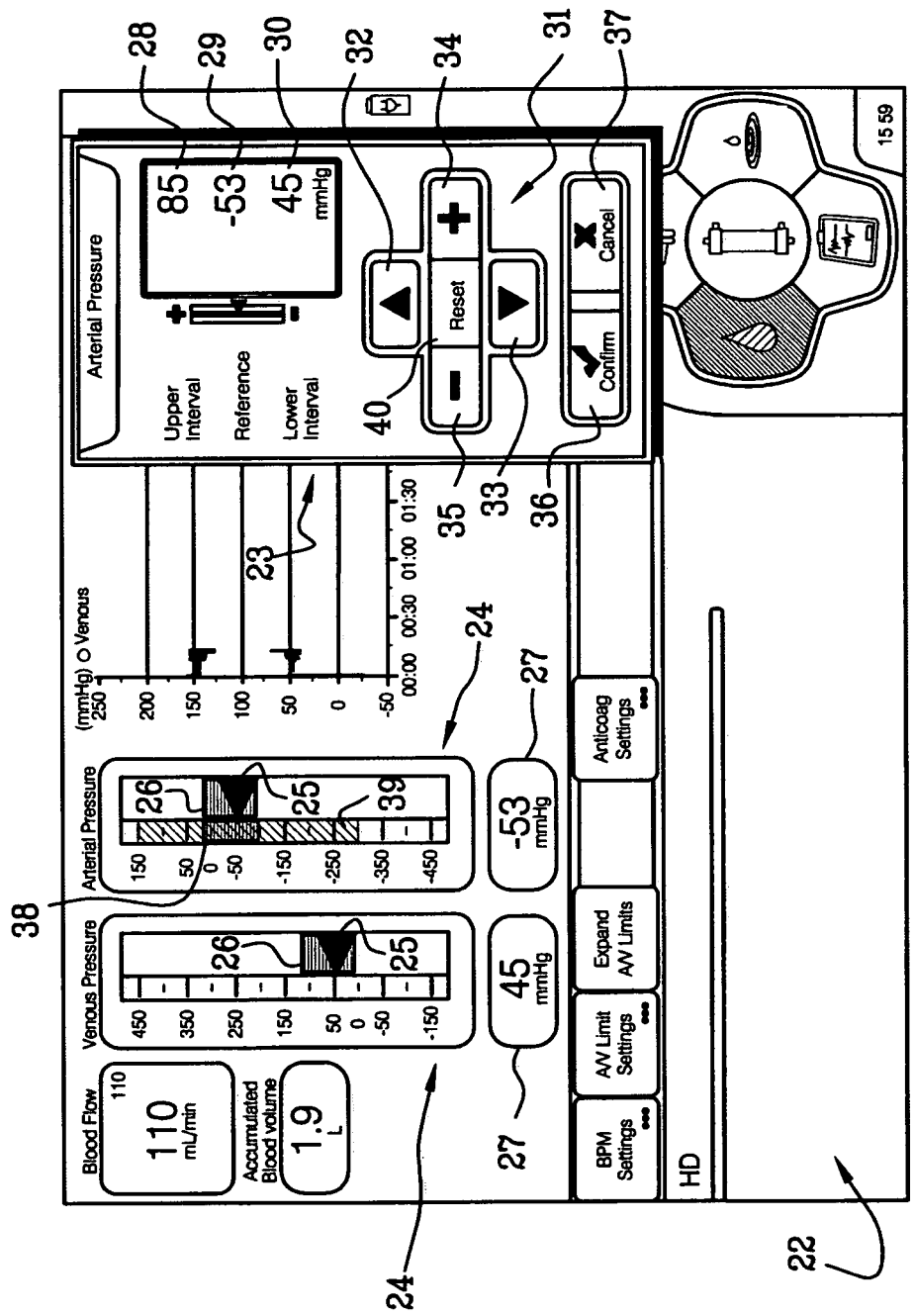

The effect of the activation of the button 33 is represented by the passage from the configuration of FIG. 3 to that of FIG. 5. In this case the upper limit of the overall safety interval has passed from +27 mmHg to +22 mmHg (the upper interval 28 having passed from 80 to 75 mmHg), while the lower limit of the safety interval has passed from −93 mmHg to −98 mmHg (the lower limit 29 having passed from 40 to 45 mmHg), while keeping the reference 29 constant at −53 mmHg.

The input means 31 comprise a broadening button 34, activation of which causes a broadening in the range of the total safety interval. In the specific case the activating of the broadening button 34 will cause an increase (by a predetermined quantity) of both the first safety value (i.e. in this case the range of the upper interval 28) and the second safety value (i.e. in this case the range of the lower interval 30), leaving the reference unaltered 29. The input means 31 comprise a narrowing button 35, activation of which causes narrowing of the width of the total safety interval. In this specific case the activation of the narrowing button 35 will cause the decreasing by a predetermined quantity of both the first safety value (i.e. in this case the range of the upper interval 28) and the second safety value (i.e. in this case the range of the lower interval 30), leaving the reference 29 unaltered. In the specific case the buttons 34 and 35 for regulating the range of the total safety interval, are provided with icons associated to the concept of range, such as for example the addition sign "+" or subtraction sign "−", or other appropriate signs (such as for example two pairs of arrows arranged such as to indicate broadening "←→" and narrowing "→←"). The effect of the activation of the narrowing button 35 is represented by the passage from the configuration of FIG. 3 to that of FIG. 6. Observe that the upper interval 28 has passed from a range of 80 mmHg to one of 75 mmHg, while the lower interval 30 has passed from a range of 40 mmHg to one of 35 mmHg. In this case the total safety interval has been narrowed by 10 mmHg. The lower limit of the total safety interval has passed from −93 mmHg to −88 mmHg, while the upper limit has passed from +27 mmHg to +22 mmHg. The reference 29 has stayed the same as the previously-measured value of −53 mmHg. The preview means (graphic representation 38) update as a consequence.

The effect of the broadening button 34 is the same but inverse (at least qualitatively if not also, optionally, from a quantitative point of view, i.e. the entity of the broadening/narrowing at each touch) to the one of the narrowing button 35. The effect is represented in the passage from the configuration of FIG. 3 to that of FIG. 7.

Thus by acting on the input means 31, which in the specific case comprise four buttons from 32 to 35, the operator can modify both the range and the position (centering) of the total safety interval. In particular the range can be modified by means of the buttons 34 and 35, while the position is modifiable by means of the buttons 32 and 33.

The use of the input means 31 is limited by one or more predefined and stored threshold values. In particular the use of the means 32 and 33 is limited by the fact that the lower limit value cannot exceed the reference value 29 (or cannot approach the reference value by more than a predetermined threshold value) and that the upper limit value cannot go below the reference value 29 (or cannot approach the reference value by more than a predetermined threshold value). In particular, the use of the means 34 and 35 is limited by a stored predefined maximum threshold value for the total interval, just as it is limited by a minimum threshold value for the total interval range.

The use of means for displacing the safety interval (i.e. in the specific case described herein, the buttons 32 and 33) is regulated (limited) on the basis of the treatment interval 39, for example in the following way: the upper limit of the safety interval cannot fall below the lower limit of the treatment interval 39 (or approach the lower limit beyond a certain possibly presettable pre-limit), while the lower limit of the safety interval cannot pass beyond (or approach beyond a certain possibly presettable pre-limit) the upper limit of the treatment interval 39. In the interest of greater safety, the control unit is configured such as to disable the input means when one of the safety threshold values is reached or is at risk of being reached and exceeded, optionally selectively i.e. by disabling only the one of the input means (in the particular case one of the buttons from 32 to 35) which would cause the exceeding of a determined threshold value.

In the above-described cases the reference 29 remains unaltered at a value measured at the moment, or before, of use of the activating means 24. It is possible to have a case in which the reference 29 is updated in real-time, or at predetermined periods, such as to correspond to the current value measured for the parameter (for example the arterial pressure or venous pressure) even during the course of the setting or modification operations of the safety interval. In this case the upper interval 28 and the lower interval 30 are in turn updated such that, by effect of a reference modification 29, the position and the range of the total safety interval are not modified but are modified by effect of a new setting performed by the operator.

The selecting means 23 comprise confirm means 36 for confirming a modification of the first and/or the second safety value. The confirm means 36 can optionally comprise a touch-button (such as in the illustrated example). The activating of the confirm means 36 leads optionally to the effective entering into the controller's memory of the selected value or values via the input means 31. The activating of the confirm means 36 optionally causes modification of the graphic representation means (in the specific case the bar graph) of the effectively set value of the safety intervals, in agreement with the new value or values entered. The activating of the confirm means 36 optionally causes the disappearance of the selecting means 23 and also, once more optionally, of the preview means (in the specific case the graphic preview representations 38 and the treatment interval 39).

The selecting means 23 comprise cancelling means 37 for cancelling a modification or a plurality of modifications of the first and/or the second safety value. The cancelling means 37 can optionally comprise a touch-button (as in the illustrated example). The activation of the cancelling means optionally causes the cancelling of all the actions performed via the input means 31 (starting from the activation of the selecting means 23 via the selecting means) or, alternatively, only of the last action performed via the input means 31. The multiple activation of the cancelling means 37 can optionally cause the reverse cancellation of the actions performed via the input means 31, in which each single activation of the cancelling means 37 cancels a single action performed via the input means 31. The activation of the cancelling means 37 can optionally cause the cancellation of the preview means (graphic representation 38 and possibly also 39).

Also included are reset means 40 (for example a touch-button which as in the specific case can be arranged at the centre of the buttons from 32 to 35 positioned in a cross fashion) the activating of which causes the reset of the setting at a determined preceding moment, for example at the initial moment of the setting, i.e. at the moment immediately following the activating of the activating means 24 of the selecting means 23. In substance, the activating of the reset means 40 causes, in the specific case, a return to the situation corresponding to the configuration of FIG. 3.

The invention claimed is:

1. An extracorporeal blood treatment apparatus comprising:
    a blood treatment device having a blood chamber and a fluid chamber separated from one another by a semipermeable membrane;
    an extracorporeal blood circuit having a removal line for sending blood from a patient to the blood chamber, and a return line for returning the blood from the blood chamber to the patient;
    a fluid circuit connected to the fluid chamber;
    one or more sensors for measuring a value of a parameter in the extracorporeal blood circuit and in the fluid circuit;
    a user interface provided with a screen and connected to the one or more sensors;
    selecting means for enabling a user to directly set, via the screen, a first safety value and a second safety value, the first safety value being greater than a reference value of the parameter, the second safety value being less than the reference value, the reference value being a measured value of the parameter, the selecting means comprising input means for modifying the first safety value and/or the second safety value, the input means comprising a first button; and
    a control unit configured to selectively disable at least part of the selecting means if one of the safety values is reached; wherein the apparatus is configured such that the first button can be activated a plurality of times in succession and, at each activation, the first safety value and the second safety value are simultaneously modified by a predetermined quantity visually on the screen; wherein, when the first button is activated and the first safety value and the second safety value are simultaneously modified, the first safety value is increased by a predetermined quantity and the second safety value is decreased by a predetermined quantity; and wherein the input means further comprises a second button, a third button and a fourth button, wherein, when the second button is activated, the first safety value is decreased by a predetermined quantity and the second safety value is increased by a predetermined quantity, and wherein, when the third button is activated, the first safety value is decreased by a predetermined quantity and the second safety value is decreased by a predetermined quantity, and wherein, when the fourth button is activated, the first safety value is increased by a predetermined quantity and the second safety value is increased by a predetermined quantity.

2. The apparatus of claim 1, wherein the selecting means comprise a video display on the screen including an alphanumeric representation of the first safety value, the reference value and the second safety value.

3. The apparatus of claim 1, wherein the input means comprise at least an increase button for increasing the first safety value, and a decrease button for reducing the first safety value.

4. The apparatus of claim 1, wherein the input means comprise at least an increase button for increasing the second safety value and a decrease button for reducing the second safety value.

5. The apparatus of claim 1, wherein the selecting means comprise means for confirming a modification of a safety value selected from the group consisting of the first safety value and the second safety value.

6. The apparatus of claim 1, wherein the user interface comprises means for activating the selecting means on the screen, the reference value being a value measured at a moment of activation of the selecting means.

7. The apparatus of claim 1, wherein the user interface comprises means for activating the selecting means on the screen, the reference value being a value measured within a predetermined period of time preceding the moment of activation.

8. The apparatus of claim 1, wherein the parameter comprises a parameter selected from a following group of parameters: an arterial pressure in the removal line, a venous pressure in the return line, a trans-membrane pressure between the blood chamber and the fluid chamber.

9. The apparatus of claim 1, wherein the selecting means comprise at least a region of a touch-screen activatable by touch/proximity.

10. The apparatus of claim 1, comprising means for graphically representing a preview of a modification of one of the safety values and means for graphically representing a current setting of said one of the safety values, the means for graphically representing the preview and the means for graphically representing the current setting being arranged side-by-side such as to present a comparative display thereof.

* * * * *